US 6,738,669 B1

(12) United States Patent
Sloman et al.

(10) Patent No.: US 6,738,669 B1
(45) Date of Patent: May 18, 2004

(54) SYSTEM AND METHOD FOR MULTICHAMBER CARDIAC STIMULATION WITH VENTRICULAR CAPTURE VERIFICATION USING FAR-FIELD EVOKED RESPONSE

(75) Inventors: Laurence S. Sloman, West Hollywood, CA (US); Kerry Bradley, Glendale, CA (US)

(73) Assignee: Pacesetter, Inc., Sylmar, CA (US)

( * ) Notice: Subject to any disclaimer, the term of this patent is extended or adjusted under 35 U.S.C. 154(b) by 448 days.

(21) Appl. No.: 10/011,127

(22) Filed: Oct. 24, 2001

Related U.S. Application Data

(63) Continuation-in-part of application No. 09/460,614, filed on Dec. 14, 1999, now Pat. No. 6,345,201, which is a continuation-in-part of application No. 09/124,811, filed on Jul. 29, 1998, now Pat. No. 6,101,416.

(51) Int. Cl.[7] ............................................. A61N 1/368
(52) U.S. Cl. ......................................... 607/28; 607/15
(58) Field of Search ..................... 607/28, 27, 13, 607/15, 9, 4, 5; 600/509, 521

(56) References Cited

U.S. PATENT DOCUMENTS

| 4,708,142 A | 11/1987 | DeCote, Jr. ........... 128/419 PT |
| 4,729,376 A | 3/1988 | DeCote, Jr. ........... 128/419 PT |
| 4,940,052 A | 7/1990 | Mann et al. |
| 4,944,298 A | 7/1990 | Sholder |
| 4,969,467 A | 11/1990 | Callaghan et al. ..... 128/419 PG |
| 5,111,811 A | * 5/1992 | Smits ........................ 128/419 |
| 5,269,319 A | * 12/1993 | Schulte et al. ............. 128/786 |
| 5,331,966 A | * 7/1994 | Bennett et al. ............ 128/696 |
| 5,350,410 A | 9/1994 | Kleks et al. ................. 607/28 |
| 5,458,623 A | 10/1995 | Lu et al. |
| 5,476,486 A | 12/1995 | Lu et al. |
| 5,534,022 A | * 7/1996 | Hoffmann et al. .......... 607/122 |
| 5,571,144 A | * 11/1996 | Schroeppel .................. 607/28 |
| 5,601,615 A | 2/1997 | Cavalli ........................ 607/28 |
| 5,683,426 A | * 11/1997 | Greenhut et al. ............... 607/9 |

(List continued on next page.)

OTHER PUBLICATIONS

Levine, et al; Assessment of Atrial Capture in Committed Atrioventricular Sequential (DVI) Pacing Systems; pp 616–623; PACE vol. 6, May–Jun. 19983, Part 1.

Levine, et al; Confirmation of Atrial Capture and Determination of Atrial Capture Thresholds in DDD Pacing Systems; pp 465–473; Clin. Prog. Pacing and Electrophysiol. 1984, vol. 2, No. 5.

Brandt, et al; Far–Field QRS Complex Sensing Via the Atrial Pacemaker Lead. I. Mechanism, Consequences, Differential Diagnosis and Countermeasures in AAI and VDD/DDD Pacing; pp 1432–1438; PACE vol. 11. Oct. 1988.

Levine; Guidelines to the Routine Evaluation and Follow–up of the Implanted Pacing System; pp 19; Siemens Pacesetter; Jan. 1993.

Primary Examiner—Kennedy Schaetzle

(57) ABSTRACT

An implantable cardiac stimulation device and method automatically verify capture of one or both ventricular chambers by sensing a far-field signal in both atrial chambers. A far-field interval window is set following the delivery of the ventricular stimulation, during which a far-field signal is detected and compared to a signal representing a predetermined far-field R-wave that represents successful capture of one or both ventricular chambers. If the far-field signal is approximately equal to the predetermined far-field R-wave signal, then capture is verified. If capture is not verified, a threshold search is performed in the ventricle in which capture was lost.

43 Claims, 10 Drawing Sheets

U.S. PATENT DOCUMENTS

| | | | |
|---|---|---|---|
| 5,683,431 A | 11/1997 | Wang | 607/28 |
| 5,713,933 A | 2/1998 | Condie et al. | 607/28 |
| 5,755,739 A * | 5/1998 | Sun et al. | 607/14 |
| 5,766,225 A * | 6/1998 | Kramm | 607/4 |
| 5,766,229 A | 6/1998 | Bornzin | 607/28 |
| 5,855,594 A | 1/1999 | Olive et al. | 607/28 |
| 5,861,012 A | 1/1999 | Stroebel | 607/28 |
| 6,101,416 A | 8/2000 | Sloman | 607/28 |
| 6,128,535 A | 10/2000 | Maarse | 607/28 |
| 6,169,921 B1 * | 1/2001 | KenKnight et al. | 607/4 |

\* cited by examiner

SYSTEM AND METHOD FOR MULTICHAMBER CARDIAC STIMULATION WITH VENTRICULAR CAPTURE VERIFICATION USING FAR-FIELD EVOKED RESPONSE

CROSS-REFERENCE TO RELATED APPLICATIONS

This application is a continuation-in-part application of U.S. patent application Ser. No. 09/460,614, filed Dec. 14, 1999, entitled "System and Method for Ventricular Capture using Far-Field Evoked Response," now U.S. Pat. No. 6,345,201 which is a continuation-in-part application of U.S. patent application Ser. No. 09/124,811, filed Jul. 29, 1998, titled "System and Method for Atrial Autocapture in Single-chamber Pacemaker Modes Using Far-Field Detection," now U.S. Pat. No. 6,101,416.

FIELD OF THE INVENTION

The present invention relates in general to implantable, cardiac electrical stimulation devices such as pacemakers or implantable cardioverter-defibrillators. In particular, this invention pertains to a system and method for detecting ventricular capture using far-field sensing of the ventricular R-wave.

BACKGROUND OF THE INVENTION

Implantable medical devices, such as pacemakers, defibrillators, cardioverters, and implantable cardioverter-defibrillators ("ICDs"), collectively referred to herein as implantable cardiac stimulating devices, are designed to monitor and stimulate the heart of a patient who suffers from a cardiac arrhythmia. Using leads connected to a patient's heart, these devices typically stimulate the cardiac muscle (myocardium) by delivering electrical pulses in response to measured cardiac events that are indicative of a cardiac arrhythmia. Properly administered therapeutic electrical pulses often successfully reestablish or maintain the heart's regular rhythm.

Implantable cardiac stimulating devices can treat a wide range of cardiac arrhythmias by using a series of adjustable parameters to alter the energy, shape, location, and frequency of the therapeutic pulses. The adjustable parameters are usually defined in a computer program stored in a memory of the implantable device. The program, which is responsible for the operation of the implantable device, can be defined or altered telemetrically by a medical practitioner using an external implantable device programmer.

Conventional programmable cardiac stimulation devices are generally of two types: (1) single-chamber, or (2) dual-chamber. In a single-chamber pacemaker, the pacemaker provides stimulation pulses to, and senses cardiac activity within, a single-chamber of the heart, either the right ventricle or the right atrium. In a dual-chamber pacemaker, the pacemaker provides stimulation pulses to, and senses cardiac activity within, two chambers of the heart, e.g., both the right atrium and the right ventricle. The left atrium and left ventricle can also be sensed and paced, provided that suitable electrical contacts are effected therewith. The recent development of multi-chamber cardiac stimulation devices allows sensing and pacing in up to all four chambers of the heart. Recent clinical evidence suggests multi-chamber stimulation may have important hemodynamic benefit in patients suffering from heart failure and may be effective in preventing arrhythmias in patients prone to sustained or frequent arrhythmias.

Cardiac stimulation devices have a great number of adjustable parameters that must be tailored to a particular patient's therapeutic needs. One adjustable parameter of particular importance is the output stimulation energy. For the stimulation device to perform its intended function, it is critically important that the delivered electrical stimuli be of sufficient energy to depolarize the cardiac tissue, a condition known as "capture".

When a pacemaker stimulation pulse stimulates either the atrium or the ventricle during an appropriate portion of a cardiac cycle, it is desirable to have the heart properly respond to the stimulus provided. Every patient has a "capture threshold" which is generally defined as the minimum amount of stimulation energy necessary to effect capture. Capture should be achieved at the lowest possible energy setting yet provide enough of a safety margin so that, should a patient's threshold increase, the output of an implantable stimulation device, i.e. the stimulation energy, will still be sufficient to maintain capture. Dual-chamber and multi-chamber stimulation devices may have differing atrial and ventricular stimulation energy that correspond to the capture thresholds of the targeted cardiac chamber.

The earliest pacemakers had a predetermined and unchangeable stimulation energy, which proved to be problematic because the capture threshold is not a static value and may be affected by a variety of physiological and other factors. For example, certain cardiac medications may temporarily raise or lower the threshold from its normal value. In another example, fibrous tissue that forms around stimulation electrodes within several months after implantation may raise the capture threshold.

As a result, some patients eventually suffered from loss of capture as their pacemakers were unable to adjust the pre-set stimulation energy to match the changed capture thresholds. One attempted solution was to set the level of stimulation pulses fairly high so as to avoid loss of capture due to a change in the capture threshold. However, this approach resulted in some discomfort to patients who were forced to endure unnecessarily high levels of cardiac stimulation. Furthermore, such stimulation pulses consumed extra battery resources, thus shortening the useful life of the pacemaker.

When programmable pacemakers were developed, the stimulation energy was implemented as an adjustable parameter that could be set or changed by a medical practitioner. Typically, such adjustments were effected by the medical practitioner using an external programmer capable of communication with an implanted pacemaker via a magnet applied to a patient's chest or via telemetry. The particular setting for the pacemaker's stimulation energy was usually derived from the results of extensive physiological tests performed by the medical practitioner to determine the patient's capture threshold, from the patient's medical history, and from a listing of the patient's medications. While the adjustable stimulation energy feature proved to be superior to the previously known fixed energy, some significant problems remained unsolved. In particular, when a patient's capture threshold changed, the patient was forced to visit the medical practitioner to adjust the stimulation energy accordingly.

To address this pressing problem, pacemaker manufacturers have developed advanced stimulation devices that are capable of determining a patient's capture threshold and automatically adjusting the stimulation pulses to a level just above that which is needed to maintain capture. This automatic capture feature improves the patient's comfort, reduces the necessity of unscheduled visits to the medical practitioner, and increases the pacemaker's battery life by conserving the energy used to generate stimulation pulses.

However, many of these advanced pacemakers require additional circuitry and/or special sensors that must be dedicated to capture verification. This requirement increases the complexity of the pacemaker system and reduces the precious space available within a pacemaker's casing, and also increases the pacemaker's cost. As a result, pacemaker manufacturers have attempted to develop automatic capture verification techniques that may be implemented in a typical programmable pacemaker without requiring additional circuitry or special dedicated sensors.

A common technique used to determine whether capture has been effected is monitoring the patient's cardiac activity and searching for the presence of an "evoked response" following a stimulation pulse. The evoked response is the response of the heart to the application of a stimulation pulse. The patient's heart activity is typically monitored by the stimulation device by keeping track of the stimulation pulses delivered to the heart and examining, through the leads connected to the heart, electrical signals that are manifest concurrent with depolarization or contraction of muscle tissue (myocardial tissue) of the heart. The contraction of atrial muscle tissue is evidenced by generation of a P-wave, while the contraction of ventricular muscle tissue is evidenced by generation of an R-wave (sometimes referred to as the "QRS" complex).

When capture occurs, the evoked response is an intracardiac P-wave or R-wave that indicates contraction of the respective cardiac tissue in response to the applied stimulation pulse. For example, using such an evoked response technique, if a stimulation pulse is applied to the ventricle, a response sensed by ventricular sensing circuits of the stimulation device immediately following the application of the stimulation pulse is presumed to be an evoked response that evidences capture of the ventricle.

However, it is for several reasons very difficult to detect a true evoked response. First, because the ventricular evoked response is a relatively small signal, it may be obscured by a high-energy stimulation pulse and therefore difficult to detect and identify. Second, the signal sensed by the stimulation device's sensing circuitry immediately following the application of a stimulation pulse may be not an evoked response but noise, such as electrical noise caused, for example, by electromagnetic interference, or myocardial noise caused by random myocardial or other muscle contraction.

Another signal that interferes with the detection of an evoked response, and potentially the most difficult for which to compensate because it is usually present in varying degrees, is lead polarization. A lead/tissue interface is that point at which an electrode of the stimulation lead contacts the cardiac tissue. Lead polarization is commonly caused by electrochemical reactions that occur at the lead/tissue interface due to application of an electrical stimulation pulse, such as a stimulation pulse, across the interface.

Because the evoked response is sensed through the same lead electrodes through which the stimulation pulses are delivered, the resulting polarization signal, also referred to as an "afterpotential", formed at the electrode can corrupt the evoked response that is sensed by the sensing circuits. This undesirable situation occurs often because the polarization signal can be three or more orders of magnitude greater than the evoked response. Furthermore, the lead polarization signal is not easily characterized; it is a complex function of the lead materials, lead geometry, tissue impedance, stimulation energy and other variables, many of which are continually changing over time.

In each of the above cases, the result may be a false positive detection of an evoked response. Such an error leads to a false capture indication, which in turn, leads to missed heartbeats, a highly undesirable and potentially life-threatening situation. In dual chamber and multichamber stimulation, successful capture all stimulated chambers is critical to maintaining proper synchrony of heart chamber contractions. Loss of optimal atrial-ventricular synchrony or inter-ventricular synchrony may have deleterious hemodynamic effects.

Another problem results from a failure by the stimulation device to detect an evoked response that has actually occurred. In that case, a loss of capture is indicated when capture is in fact present, also an undesirable situation that will cause the device to unnecessarily deliver a high-energy back-up stimulation pulse and invoke the threshold search function in a chamber of the heart.

Automatic threshold testing is invoked by the stimulation device when loss of ventricular capture is detected or on a predetermined periodic basis. An exemplary threshold test is performed as follows. When loss of capture is detected, the device increases the stimulation pulse energy to a relatively high predetermined testing level at which capture is certain to occur, and thereafter decrements the output energy until capture is lost. The stimulation energy is then set to a level slightly above the lowest output energy at which capture was still detected. Thus, capture verification is of utmost importance in proper determination of the stimulation energy.

When a ventricular stimulation pulse is properly captured in the ventricle, a subsequent ventricular contraction results in an R-wave which may be sensed through an atrial lead, in patients with intact atrioventricular ("AV") conduction, as a "far-field" signal, also referred to herein as "far-field R-wave" or "far-field evoked response". The far-field R-wave confirms successful ventricular capture because the ventricular contraction only occurs after a properly captured ventricular stimulation pulse.

However, previously known dual-chamber and multichamber pacemakers do not sense ventricular activity through the atrial lead for a particular interval of time (i.e., the "post-ventricular atrial refractory period," commonly known as PVARP) subsequent to the delivery of the ventricular stimulation pulse. This refractory period on the atrial channel following ventricular stimulation prevents the atrial channel from mistaking a far-field R-wave for an atrial P-wave. However, detection of the far-field R-wave can be advantageous in verifying that ventricular capture has occurred.

It would thus be desirable to provide a system and method for automating the detection of capture on one or both ventricular channels of an implantable multi-chamber stimulation device, with increased accuracy. It would also be desirable to provide a system and method for reducing the negative effect of polarization and noise on capture verification. It would further be desirable to enable the stimulation device to perform ventricular capture verification without requiring dedicated circuitry and/or special sensors.

SUMMARY OF THE INVENTION

The present invention addresses these needs by providing a system and method for automatically detecting capture of a ventricular chamber in a multi-chamber cardiac stimulation device. Ventricular capture is detected by sensing the far-field R-wave that follows a ventricular stimulation pulse that has successfully captured the ventricle.

In one illustrative embodiment of the invention, the device delivers a ventricular stimulation pulse to both the right and left ventricles and then samples a far-field R-wave, resulting from the biventricular evoked response, on the atrial channel during a predetermined far-field interval window.

In another illustrative embodiment, the device delivers a ventricular stimulation pulse to one ventricle and then samples a far-field evoked response on a pair of atrial channels during a predetermined far-field interval window.

In certain embodiments, capture may be verified by comparing one or more signal characteristics of the far-field R-wave sample, such as peak amplitude, integral, or slope, to the same characteristic(s) of an expected far-field R-wave following an evoked response in the designated ventricle.

BRIEF DESCRIPTION OF THE DRAWINGS

Further features and advantages of the present invention may be more readily understood by reference to the following description taken in conjunction with the accompanying drawings, in which.

DETAILED DESCRIPTION OF THE PREFERRED EMBODIMENTS

The following description is of the best mode presently contemplated for practicing the invention. This description is not to be taken in a limiting sense but is made merely for the purpose of describing the general principles of the invention. The scope of the invention should be ascertained with reference to the issued claims. In the description of the invention that follows, like numerals or reference designators will be used to refer to like parts or elements throughout.

As indicated earlier, it is an object of the present invention is to provide a multichamber cardiac stimulation device capable of reliably performing ventricular capture verification by detecting an evoked response from sensed far-field signals. The methods for verifying capture in accordance with the present invention will be described in detail in conjunction with FIGS. 3–9. These methods may be implemented in numerous multichamber cardiac stimulation devices, possessing one or more ventricular leads and one or more atrial leads. A preferred embodiment of a multichamber cardiac stimulation device will first be described in conjunction with FIGS. 1 and 2.

Figure 1:
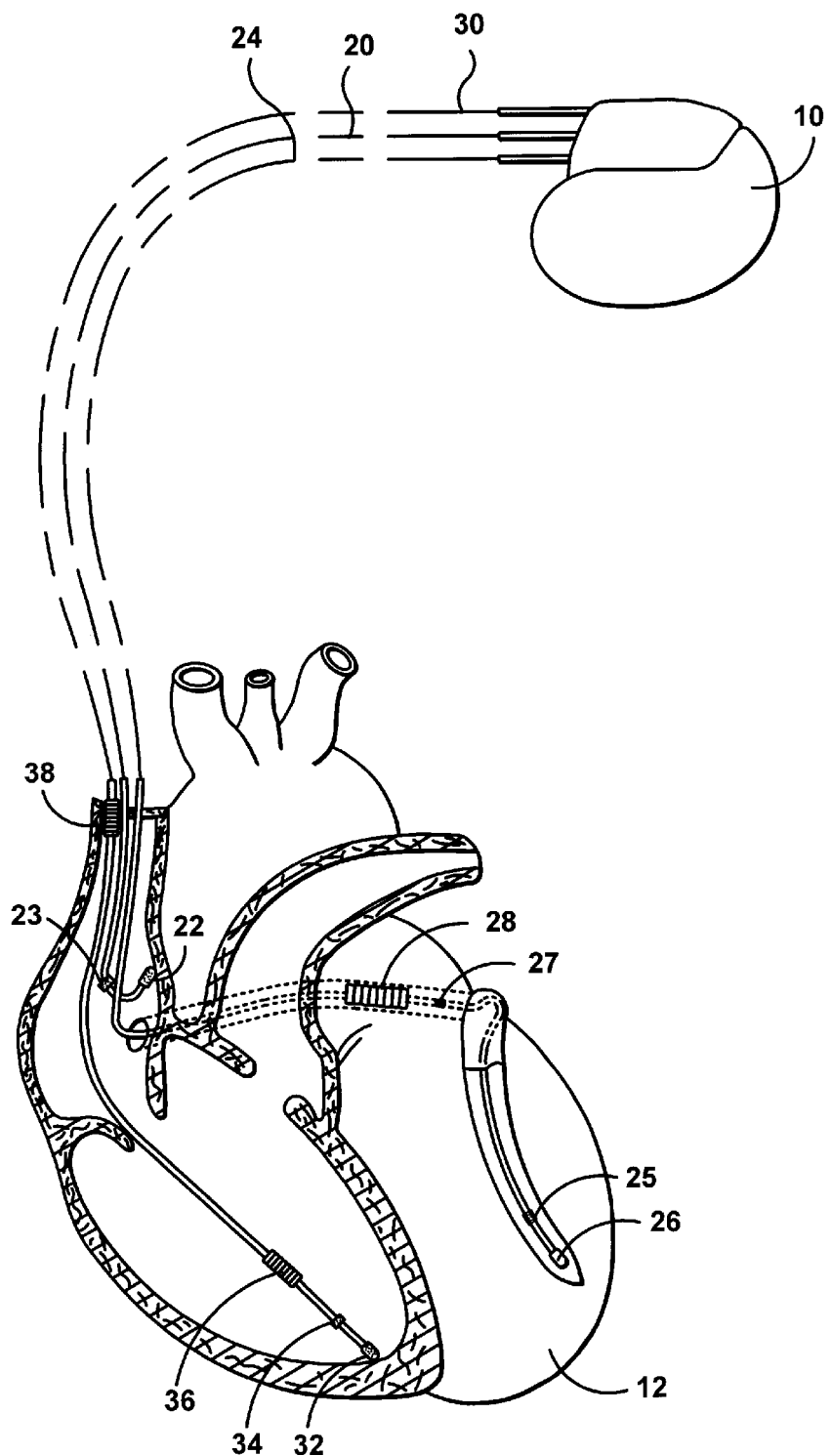
FIG. 1 is a simplified diagram illustrating an implantable stimulation device in electrical communication with at least three leads implanted into a patient's heart for delivering multi-chamber stimulation and shock therapy.

As shown in FIG. 1, there is a stimulation device 10 in electrical communication with a patient's heart 12 by way of three leads, 20, 24 and 30, suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage.

To sense left atrial and ventricular cardiac signals and to provide left chamber stimulation therapy, the stimulation device 10 is coupled to a "coronary sinus" lead 24 designed for placement in the "coronary sinus region" via the coronary sinus osmium for positioning a distal electrode adjacent to the left ventricle and/or additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, an exemplary coronary sinus lead 24 is designed to receive atrial and ventricular cardiac signals and to deliver left ventricular stimulation therapy using at least a left ventricular tip electrode 26, left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and an SVC coil electrode 38. Typically, the right ventricular lead 30 is transvenously inserted into the heart 12 so as to place the right ventricular tip electrode 32 in the right ventricular apex so that the RV coil electrode will be positioned in the right ventricle and the SVC coil electrode 38 will be positioned in the superior vena cava. Accordingly, the right ventricular lead 30 is capable of receiving cardiac signals, and delivering stimulation in the form of pacing and shock therapy to the right ventricle.

Figure 2:
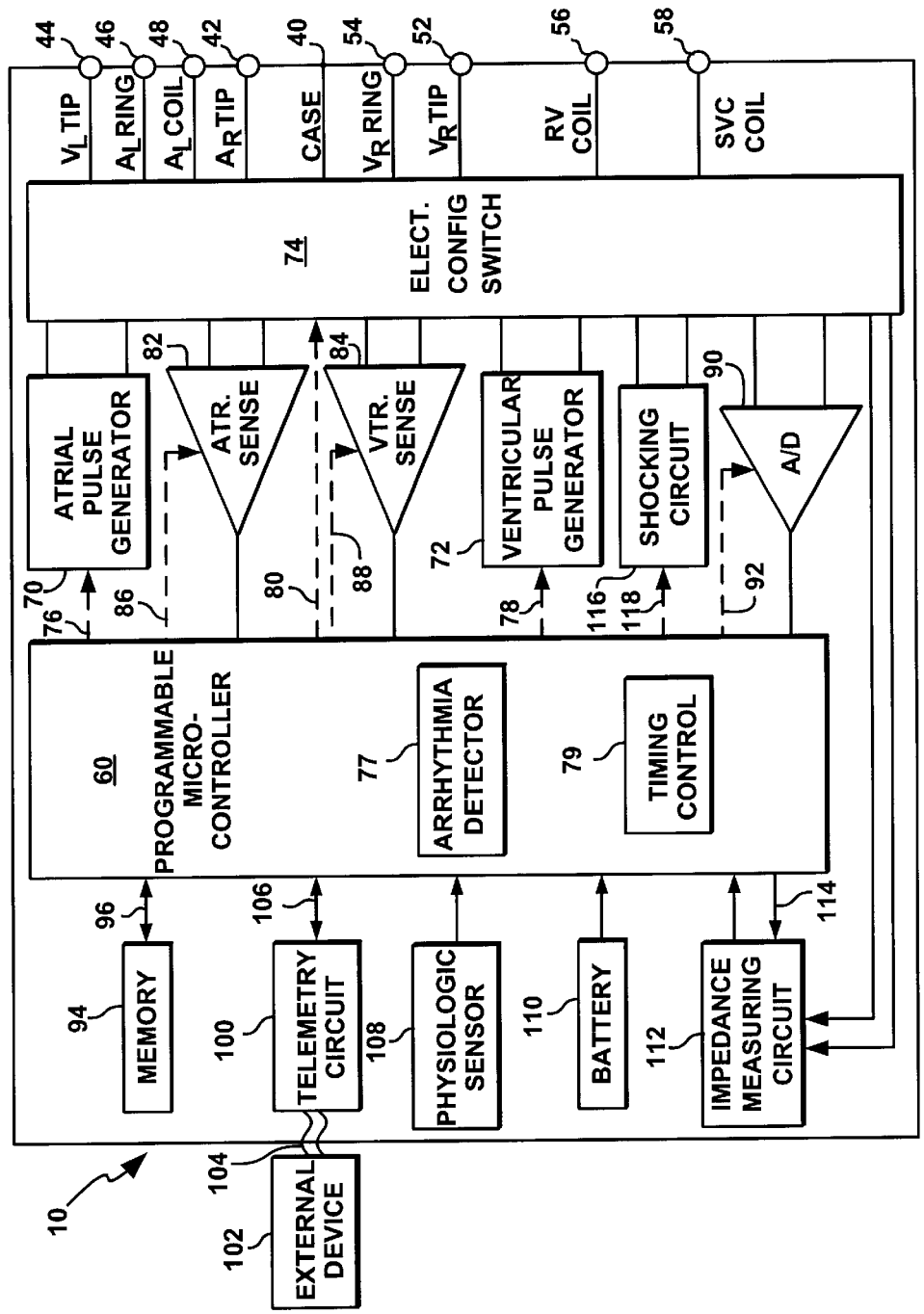
FIG. 2 is a functional block diagram of a multi-chamber implantable stimulation device illustrating the basic elements of a stimulation device which can provide cardioversion, defibrillation and pacing stimulation in four chambers of the heart.

As illustrated in FIG. 2, a simplified block diagram is shown of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The housing 40 for the stimulation device 10, shown schematically in FIG. 2, is often referred to as the "can", "case" or "case electrode" and may be programmably selected to act as the return electrode for all "unipolar" modes. The housing 40 may further be used as a return electrode alone or in combination with one or more of the coil electrodes, 28, 36 and 38, for shocking purposes. The stimulation device 10 further includes a connector having a plurality of terminals, 42, 44, 46, 48, 52, 54, 56, and 58 (shown schematically and, for convenience, the names of the electrodes to which they are connected are shown next to the terminals). As such, to achieve right atrial sensing and pacing, the connector includes at least a right atrial tip terminal ($A_R$ TIP) 42 adapted for connection to the atrial tip electrode 22.

To achieve left chamber sensing, pacing and shocking, the connector includes at least a left ventricular tip terminal ($V_L$ TIP) 44, a left atrial ring terminal ($A_L$ RING) 46, and a left atrial shocking terminal ($A_L$ COIL) 48, which are adapted for connection to the left ventricular ring electrode 26, the left atrial tip electrode 27, and the left atrial coil electrode 28, respectively.

To support right chamber sensing, pacing and shocking, the connector further includes a right ventricular tip terminal ($V_R$ TIP) 52, a right ventricular ring terminal ($V_R$ RING) 54, a right ventricular shocking terminal ($R_V$ COIL) 56, and an SVC shocking terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 which controls the various modes of stimulation therapy. The microcontroller 60 typically includes a microprocessor, or equivalent control circuitry, designed specifically for controlling the delivery of stimulation therapy and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. Any suitable microcontroller 60 may be used that carries out the functions described herein.

As shown in FIG. 2, an atrial pulse generator 70 and a ventricular pulse generator 72 generate stimulation pulses for delivery by the right atrial lead 20, the right ventricular lead 30, and/or the coronary sinus lead 24 via an electrode configuration switch 74. It is understood that in order to provide stimulation therapy in each of the four chambers of the heart, the atrial and ventricular pulse generators, 70 and 72, may include dedicated, independent pulse generators, multiplexed pulse generators, or shared pulse generators. The pulse generators, 70 and 72, are controlled by the microcontroller 60 via appropriate control signals, 76 and 78, respectively, to trigger or inhibit the stimulation pulses. As used herein, the shape of the stimulation pulses is not limited to an exact square or rectangular shape, but may assume any one of a plurality of shapes which is adequate for the delivery of an energy pulse, packet, or stimulus.

The microcontroller 60 further includes timing control circuitry 79 which is used to control the timing of such stimulation pulses (e.g., pacing rate, atrio-ventricular (AV) delay, atrial interconduction (A—A) delay, or ventricular interconduction (V—V) delay, etc.) as well as to keep track of the timing of refractory periods, blanking intervals, noise detection windows, evoked response windows, alert intervals, marker channel timing, etc.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, cross-chamber, etc.) by selectively closing the appropriate combination of switches.

Atrial sensing circuits 82 and ventricular sensing circuits 84 may also be selectively coupled to the right atrial lead 20, coronary sinus lead 24, and the right ventricular lead 30, through the switch 74 for detecting the presence of cardiac activity in each of the four chambers of the heart. Accordingly, the atrial (ATR. SENSE) and ventricular (VTR. SENSE) sensing circuits, 82 and 84, may include dedicated sense amplifiers, multiplexed amplifiers, or shared amplifiers. The switch 74 determines the "sensing polarity" of the cardiac signal by selectively closing the appropriate switches. In this way, the clinician may program the sensing polarity independent of the stimulation polarity.

Furthermore, in a preferred embodiment of the present invention, the sensing polarity during ventricular capture verification may be programmed independently of the sensing polarity during normal device 10 operation. During normal operation, stimulation may be delivered in a demand or triggered mode based on the detection (or lack of detection) of intrinsic R-waves and P-waves. However, once ventricular stimulation is delivered, and automatic capture is enabled, ventricular capture verification is performed, according to the present invention, by sensing a far-field R-wave rather than a local R-wave. Therefore, one sensing polarity may be programmed for detecting local intrinsic activity and an independent sensing polarity may be programmed for detecting far-field R-waves during ventricular capture verification.

Each sensing circuit, 82 and 84, preferably employs one or more low power, precision amplifiers with programmable gain and/or automatic gain control, bandpass filtering, and a threshold detection circuit to selectively sense the cardiac signal of interest. The automatic gain control enables the device 10 to deal effectively with the difficult problem of sensing the low amplitude signal characteristics of atrial or ventricular fibrillation.

The outputs of the atrial and ventricular sensing circuits, 82 and 84, are connected to the microcontroller 60 which, in turn, are able to trigger or inhibit the atrial and ventricular pulse generators, 70 and 72, respectively, in a demand fashion in response to the absence or presence of cardiac activity in the appropriate chambers of the heart. The sensing circuits, 82 and 84, in turn, receive control signals over signal lines, 86 and 88, from the microcontroller 60 for purposes of controlling the gain, threshold, polarization charge removal circuitry, and the timing of any blocking circuitry coupled to the inputs of the sensing circuits, 82 and 86

For arrhythmia detection, the stimulation device 10 includes an arrhythmia detector 77 that utilizes the atrial and ventricular sensing circuits, 82 and 84, to sense cardiac signals to determine whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (i.e., bradycardia, normal, low rate VT, high rate VT, and fibrillation rate zones) and various other characteristics (e.g., sudden onset, stability, physiologic sensors, and morphology, etc.) in order to determine the type of remedial therapy that is needed (e.g., bradycardia pacing, anti-tachycardia pacing, cardioversion shocks or defibrillation shocks, collectively referred to as "tiered therapy").

Cardiac signals are also applied to the inputs of an analog-to-digital (A/D) data acquisition system 90. The data acquisition system 90 is configured to acquire intracardiac electrogram signals, convert the raw analog data into a digital signal, and store the digital signals for later processing and/or telemetric transmission to an external device 102. The data acquisition system 90 is coupled to the right atrial lead 20, the coronary sinus lead 24, and the right ventricular lead 30 through the switch 74 to sample cardiac signals across any pair of desired electrodes.

Advantageously, the data acquisition system 90 may be coupled to the microcontroller, or other detection circuitry, for detecting an evoked response from the heart 12 in response to an applied stimulus, thereby aiding in the detection of "capture".

In one embodiment of the present invention, the analog-to-digital acquisition system 90 is used to sample and store far-field R-wave signals for defining a far-field R-wave template and to allow comparison of a sampled far-field signals to a far-field R-wave template or signal characteristic in order to confirm capture. The capture detection methods included in the present invention will be described in detail in conjunction with FIGS. 3 through 9.

Capture occurs when an electrical stimulus applied to the heart is of sufficient energy to depolarize the cardiac tissue, thereby causing the heart muscle to contract. The microcontroller 60 detects a depolarization signal during a window following a stimulation pulse, the presence of which indicates that capture has occurred. The microcontroller 60 enables capture detection by triggering the ventricular pulse generator 72 to generate a stimulation pulse, starting a capture detection window using the timing control circuitry 79 within the microcontroller 60, and enabling the data acquisition system 90 via control signal 92 to sample the cardiac signal that falls in the capture detection window and, based on the amplitude, determines if capture has occurred.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, pacing pulse amplitude, pulse duration, electrode polarity, rate, sensitivity, automatic features, arrhythmia detection criteria, and the amplitude, waveshape and vector of each shocking pulse to be delivered to the patient's heart 12 within each respective tier of therapy. A feature of the present invention is the ability to sense and store a relatively large amount of data (e.g., from the data acquisition system 90), which data may then be used for subsequent analysis to guide the programming of the device.

Advantageously, the operating parameters of the implantable device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller by a control signal 106. The telemetry circuit 100 advantageously allows intracardiac electrograms and status information relating to the operation of the device 10 (as contained in the microcontroller 60 or memory 94) to be sent to the external device 102 through an established communication link 104.

In the preferred embodiment, the stimulation device 10 further includes a physiologic sensor 108, commonly referred to as a "rate-responsive" sensor because it is typically used to adjust pacing stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various pacing parameters (such as rate, AV Delay, V—V Delay, etc.) at which the atrial and ventricular pulse generators, 70 and 72, generate stimulation pulses.

While shown as being included within the stimulation device 10, it is to be understood that the physiologic sensor 108 may also be external to the stimulation device 10, yet still be implanted within or carried by the patient. A common type of rate responsive sensor is an activity sensor, such as an accelerometer or a piezoelectric crystal, which is mounted within the housing 40 of the stimulation device 10.

Other types of physiologic sensors are also known, for example, sensors which sense the oxygen content of blood, respiration rate and/or minute ventilation, pH of blood, ventricular gradient, etc. However, any sensor may be used which is capable of sensing a physiological parameter which corresponds to the exercise state of the patient.

The stimulation device additionally includes a battery 110 which provides operating power to all of the circuits shown in FIG. 2. For the stimulation device 10, which employs shocking therapy, the battery 110 should be capable of operating at low current drains for long periods of time, and then be capable of providing high-current pulses (for capacitor charging) when the patient requires a shock pulse. The battery 110 should also have a predictable discharge characteristic so that elective replacement time can be detected.

As further shown in FIG. 2, the device 10 is shown as having an impedance measuring circuit 112 which is enabled by the microcontroller 60 via a control signal 114. The known uses for an impedance measuring circuit 120 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 120 is advantageously coupled to the switch 74 so that any desired electrode may be used.

In the case where the stimulation device 10 is intended to operate as an implantable cardioverter/defibrillator (ICD) device, it must detect the occurrence of an arrhythmia, and automatically apply an appropriate electrical shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high energy (11 to 40

Joules), as controlled by the microcontroller 60. Such shocking pulses are applied to the patient's heart 12 through at least two shocking electrodes, and as shown in this embodiment, selected from the left atrial coil electrode 28, the RV coil electrode 36, and/or the SVC coil electrode 38. As noted above, the housing 40 may act as an active electrode in combination with the RV electrode 36, or as part of a split electrical vector using the SVC coil electrode 38 or the left atrial coil electrode 28 (i.e., using the RV electrode as a common electrode).

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
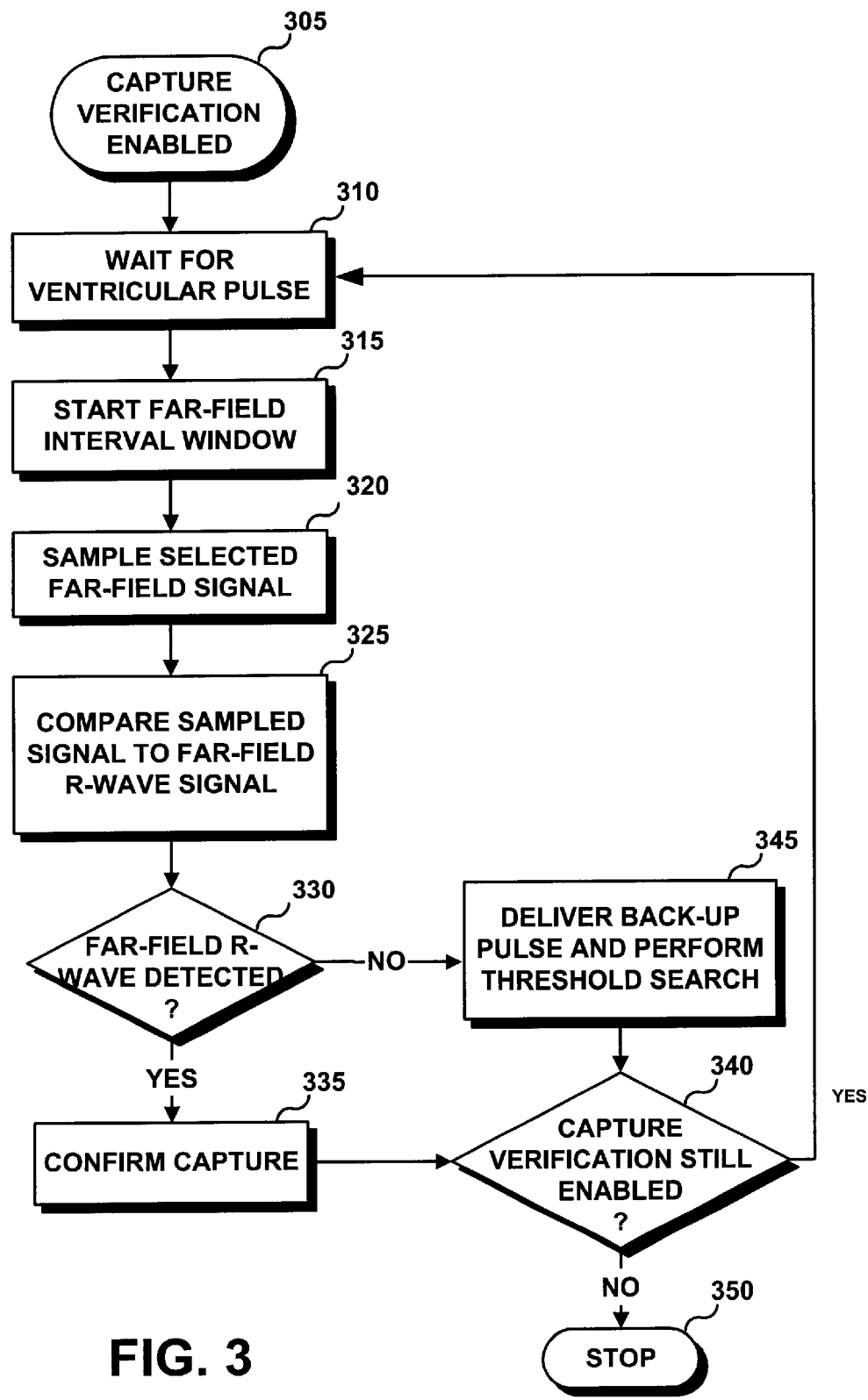
FIG. 3 is a flow chart describing an overview of the operation of one embodiment of the present invention for verifying ventricular capture by sensing far-field signals.

In FIG. 3, a flow chart is shown describing an overview of the operation and novel features implemented in one embodiment of the device 10. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

Figure 4:
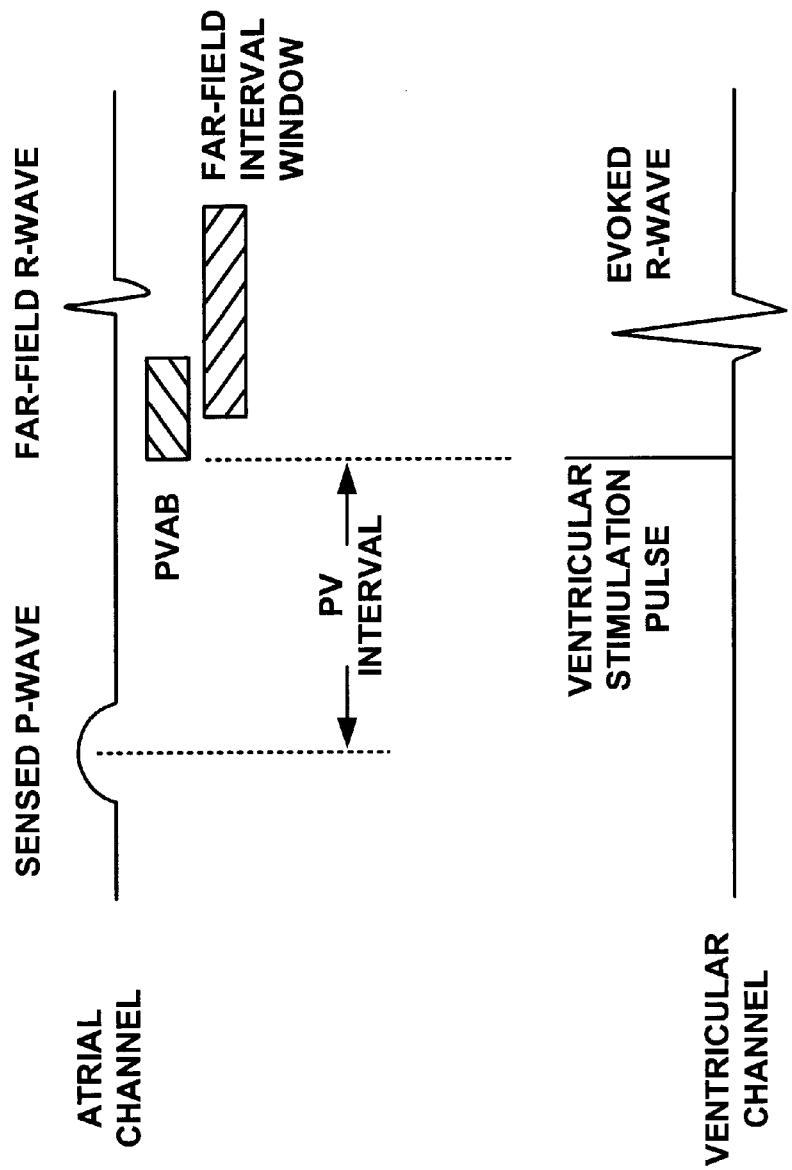
FIG. 4 is a timing diagram of an atrial channel and a ventricular channel illustrating the ventricular capture verification process of FIG. 3 using detection of a far-field R-wave in an atrial chamber.

The flow chart of FIG. 3 represents a control program 300 for performing automatic ventricular capture verification. At step 305, the automatic capture verification feature of device 10 is enabled. The control program 300 waits for a ventricular stimulation pulse to be delivered at step 310. The stimulation may be delivered in the right ventricle, the left ventricle, or both ventricles depending on how device 10 is programmed to operate. With further reference to FIG. 4, the ventricular stimulation pulse(s) may be delivered upon expiration of an AV or PV interval following either an atrial stimulation pulse or atrial sensed P-wave, respectively. In FIG. 4, a ventricular stimulation pulse is shown to be delivered following a PV interval after an atrial P-wave has been sensed. The ventricular stimulation pulse(s) may also be delivered in a ventricular demand, atrial non-tracking mode, depending on the current operating conditions of the device 10.

Referring again to FIG. 3, upon delivery of a ventricular stimulation pulse, the control program 300 starts a far-field interval window at step 315. The far-field interval window is defined by two parameters: a far-field interval delay following the ventricular stimulation pulse, and a far-field interval duration.

The far-field interval delay may be a fixed value, for example 15 msec, stored in memory 94 or it may be a programmable variable determined from measurements of the ventricular-atrial (VA) conduction time. Methods known or available in the art may be used to measure the ventricular-atrial conduction time so that the far-field interval delay may be programmed appropriately by a clinician to occur after the ventricular stimulation pulse but before the expected far-field signal. The ventricularatrial conduction time may also be determined automatically as will be described later in conjunction with FIGS. 8 and 9, so that the far-field interval delay may be programmed automatically.

The far-field interval window duration is preferably a programmable setting and is typically on the order of 100 msec. The duration should be sufficiently long enough to allow the far-field signal to be sampled. As illustrated in FIG. 4, the ventricular stimulation pulse is followed immediately by a post-ventricular atrial blanking period (PVAB) and, after a short delay, a far-field interval window during which a far-field R-wave occurs.

The desired far-field signal is sampled during the far-field interval window at step 320 (FIG. 3). The far-field signal to be sampled is selected based upon the type of ventricular stimulation delivered (right, left or biventricular) and the far-field signal characterized by the best signal-to-noise ratio. For example if right ventricular stimulation is delivered, a far-field signal may be sensed either in either a unipolar or bipolar fashion using any combination of electrodes from right atrial lead 20 or from coronary sinus lead 24. If far-field sensing is performed using the coronary sinus lead 24, the left atrial ring electrode 27 and/or left atrial coil electrode 28 positioned in the region of the left atrium may be used to detect a far-field evoked response arising from the right ventricle in the left atrium. If only the right ventricle is stimulated, the left ventricular tip electrode 26 of coronary sinus lead 24 may also be used for detecting the far-field evoked response signal arising from the right ventricle in the left ventricle. Thus, during right ventricular stimulation, capture verification may be performed by sensing the far-field R-wave in the right atrium, the left atrium, or the left ventricle. During biventricular stimulation, the farfield R-wave may be sensed in the right atrium or the left atrium; during left ventricular stimulation, the far-field R-wave may be sensed in the right or left atrium or the right ventricle.

Of the far-field sensing sites available, the sensing configuration providing the highest far-field R-wave amplitude relative to signal noise is preferably selected as the sensing configuration for ventricular capture verification. Therefore, at step 320, the desired sensing electrode configuration for the type of ventricular stimulation delivered (left, right or biventricular), is selectively connected through switch 74. The far-field signal is then received by the appropriate sensing circuitry, either the atrial sensing circuit 82 or the ventricular sensing circuit 84, and sampled and stored by the A/D converter 90.

In one embodiment, the sampled signal is compared, at step 325, to a far-field R-wave signal characteristic stored in memory 94. Standard methods known or available in the art for comparing the peak amplitude, the integral, the slope or another characteristic feature of an evoked R-wave to an expected value may be used to determine if the sampled far-field signal is indeed a far-field R-wave. Alternatively, the morphology of the sampled signal may be compared to the morphology of a far-field R-wave template, stored in memory 94. A far-field R-wave template may be supplied by a medical practitioner using the external device 102 or, preferably, may be automatically determined according to a control program executed by microcontroller 60. The details describing the acquisition of a far-field R-wave template will explained in conjunction with FIGS. 5 through 9.

If the control program 300 determines at decision step 330 that the sampled signal characteristic is approximately equal to a far-field R-wave signal characteristic, or that the sampled signal approximately matches a far-field R-wave signal template, a far-field R-wave is deemed detected, and capture is confirmed at step 335. If a far-field R-wave is not detected because the sample signal differs from the capture detection criteria, the control program 300 delivers a back-up stimulation pulse and initiates a threshold search algorithm. The threshold search algorithm redetermines the capture threshold at the present time and adjusts the stimulation pulse energy accordingly to regain capture.

As long as the automatic capture verification feature remains enabled, as determined at decision step 340, the control program 300 returns to step 310 to await the next ventricular stimulation pulse. If the capture verification feature becomes disabled, for example by a medical practitioner delivering a command using an external programmer, the control program 300 is terminated at step 350.

Figure 10:
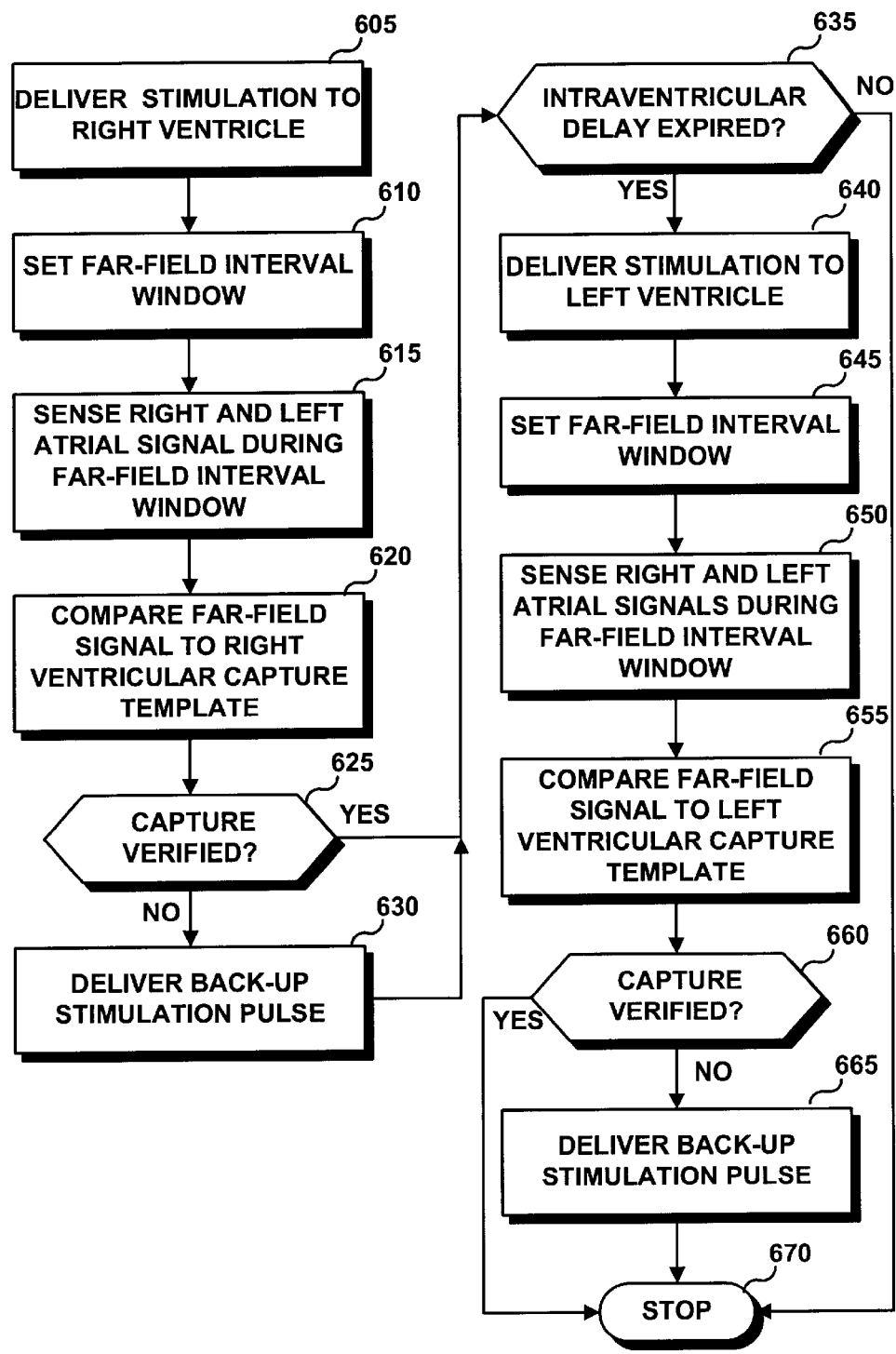
FIG. 10 is a flow chart depicting an alternative method for verifying ventricular capture by sensing far-field signals in both the right and left atria.

In a preferred embodiment for use in the system shown in FIG. 1, a ventricular stimulation pulse is delivered first in one ventricle, either left or right, and the far-field signal is sensed from both the right and left atria to verify capture of the first ventricle. A ventricular stimulation pulse may then be delivered to the second ventricle at a predetermined time interval following stimulation of the first ventricle. A far-field signal is then sensed from both the right and left atria to verify capture of the second ventricle. These steps are outlined in the flow chart shown in FIG. 10.

At step 605, a ventricular stimulation pulse is delivered to one ventricle, in this example, the right ventricle. A far-field interval window is set at step 610 following the ventricular stimulation pulse, and the right and left atrial signal is sampled during the far-field interval window at step 615. The sampled right and left atrial signal is compared to a far-field R-wave template at step 620 representing a far-field evoked response for the right ventricle. If the sampled signal approximately matches the template, capture is verified at decision step 625. If not, a back-up stimulation pulse is delivered at step 630.

Next, device 10 waits for an intra-ventricular delay to expire at decision step 635. If the intra-ventricular delay does not expire without sensing an intrinsic R-wave in the second ventricle, in this example the left ventricle, then no stimulation pulse is delivered to the left ventricle and the algorithm is terminated for the present cardiac cycle at step 670. If the intraventricular delay does expire without sensing an intrinsic R-wave, a ventricular stimulation pulse is delivered in the left ventricle at step 640. A far-field interval window is set at step 645, and the right and left atrial signal is sampled during the window at step 650. The sampled signal is compared to a far-field R-wave template representing a far-field evoked response in the left ventricle at step 655. If the sampled signal approximately matches the template, capture is verified at step 660, and the algorithm is terminated at step 670. If capture is not verified, a back-up stimulation pulse is delivered in the left ventricle at step 665 after which the algorithm is terminated at step 670 for the present cardiac cycle.

Figure 5:
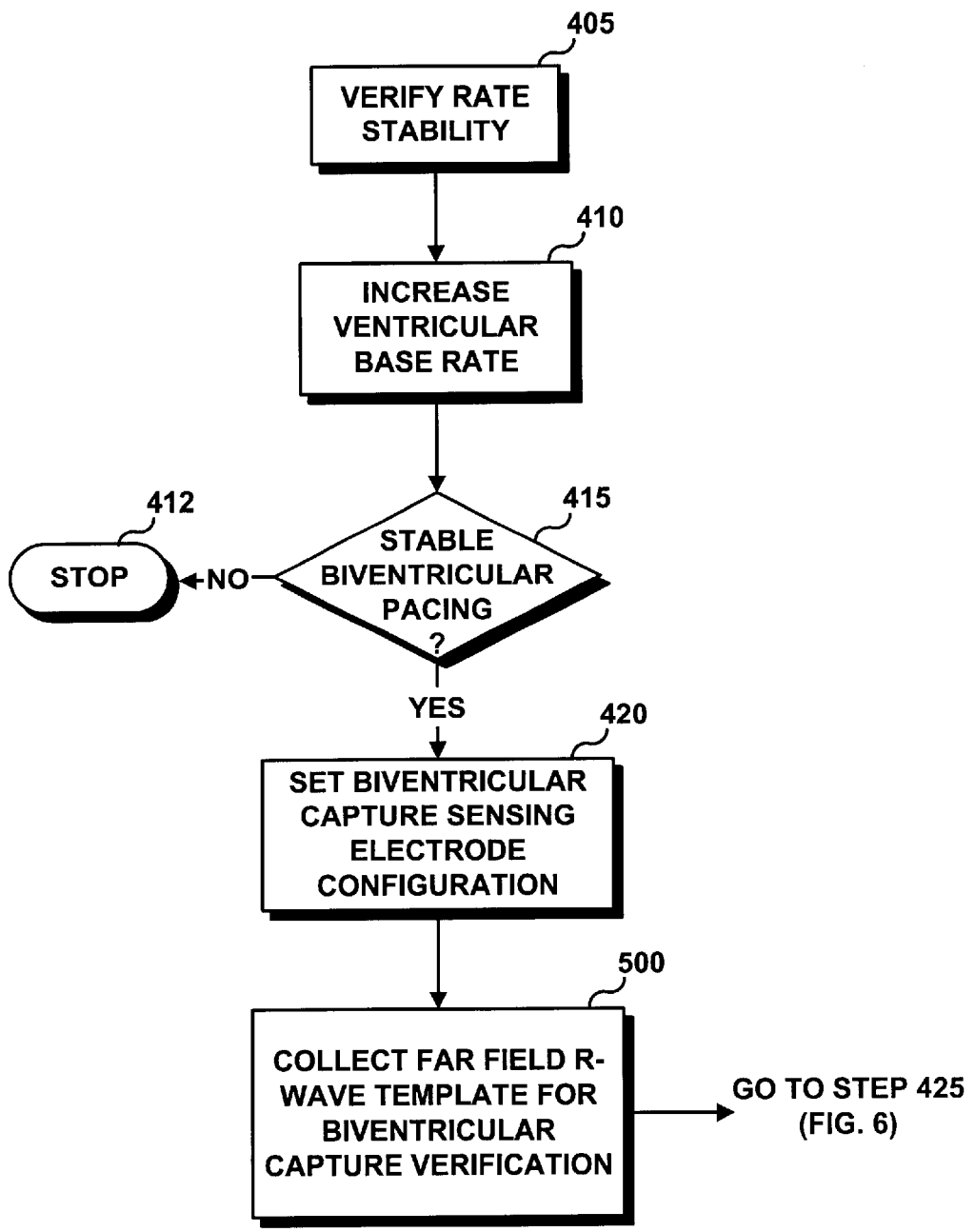
FIG. 5 is a flow chart depicting a method for determining a far-field R-wave template during biventricular stimulation to be used in the operations of FIG. 3.
Figure 6:
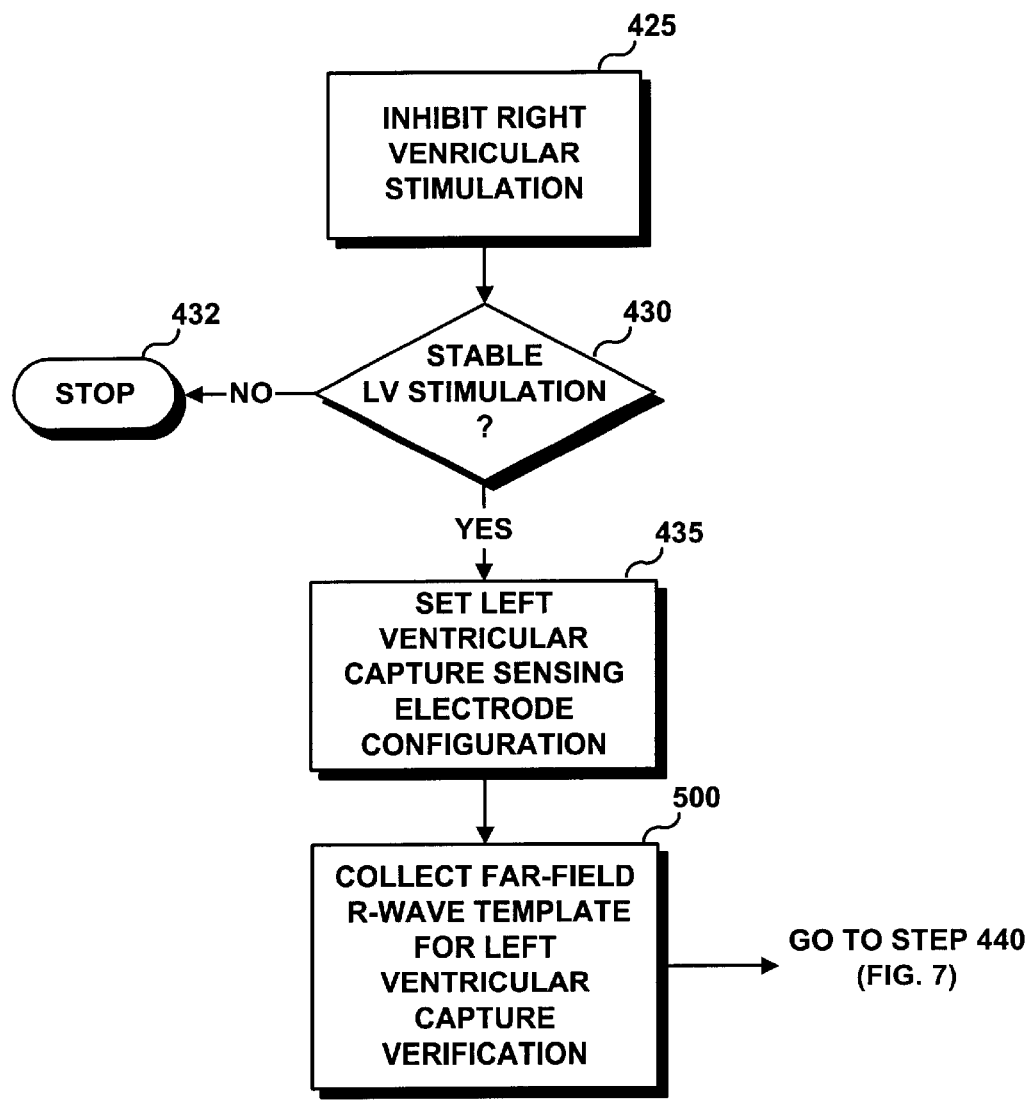
FIG. 6 is a flow chart depicting a method for determining a far-field R-wave template during left ventricular stimulation to be used in the operations of FIG. 3.
Figure 7:
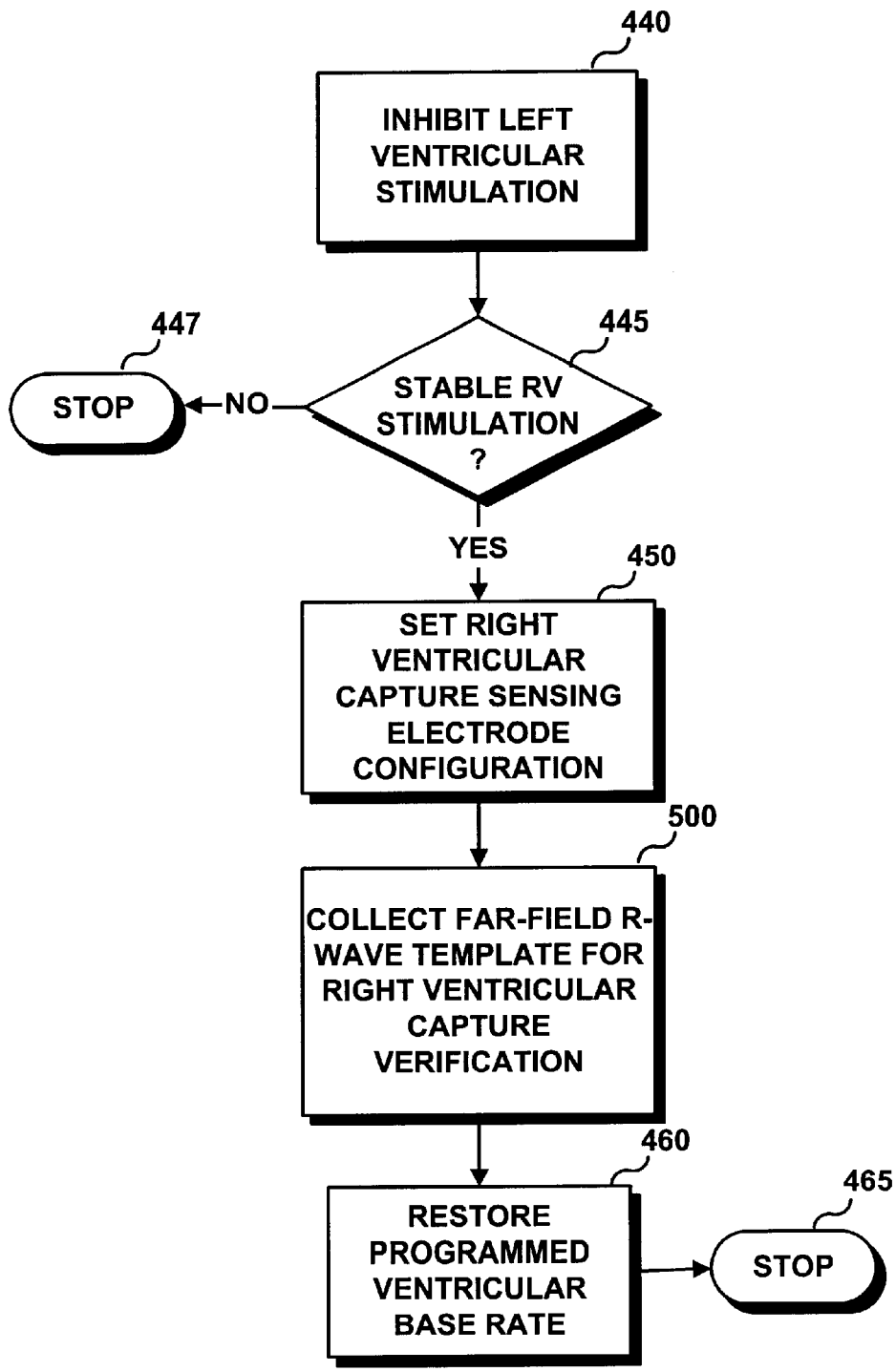
FIG. 7 is a flow chart depicting a method for determining a far-field R-wave template during right ventricular stimulation to be used in the operations of FIG. 3.

In FIGS. 5 through 7, the methods by which a far-field R-wave signal may be collected for the purposes of defining a far-field R-wave template during biventricular stimulation (FIG. 5), left ventricular stimulation (FIG. 6), and right ventricular stimulation (FIG. 7) are shown. Referring first to FIG. 5, at step 405, the ventricular rate is verified as being a stable, non-arrhythmic rate. At step 410, the ventricular base rate is increased by a predefined amount to ensure biventricular stimulation. If stable biventricular stimulation does not occur, as determined at decision step 415, the method 400 is terminated at step 412. If stable biventricular stimulation is established and maintained, the desired biventricular capture sensing electrode configuration is selected at step 420. At step 500, the far-field R-wave signal template is collected according to the methods to be described in conjunction with FIGS. 8 and 9.

Method 400 then proceeds to step 425 (FIG. 6). The stimulation output to the right ventricle is inhibited at step 425 to allow stable left ventricular (LV) stimulation only. If stable left ventricular stimulation is not established as determined at decision step 430, the method 400 is terminated at step 432. If stable left ventricular stimulation is established, the left ventricular capture sensing electrode configuration is selected at step 435. At step 500, the far-field R-wave signal template is collected according to the methods to be described in conjunction with FIGS. 8 and 9.

Method 400 then proceeds to step 440 (FIG. 7) where the left ventricular stimulation output is temporarily inhibited to establish only right ventricular stimulation. If stable right ventricular (RV) stimulation is not established at decision step 445, the method 400 is terminated at step 447. Otherwise, method 400 continues to step 450 by selecting the desired right ventricular capture sensing electrode configuration. At step 500, the far-field R-wave signal template is collected for right ventricular capture verification as will be described next. The programmed ventricular base rate is then restored at step 460 and method 400 is terminated at step 465.

Figure 8:
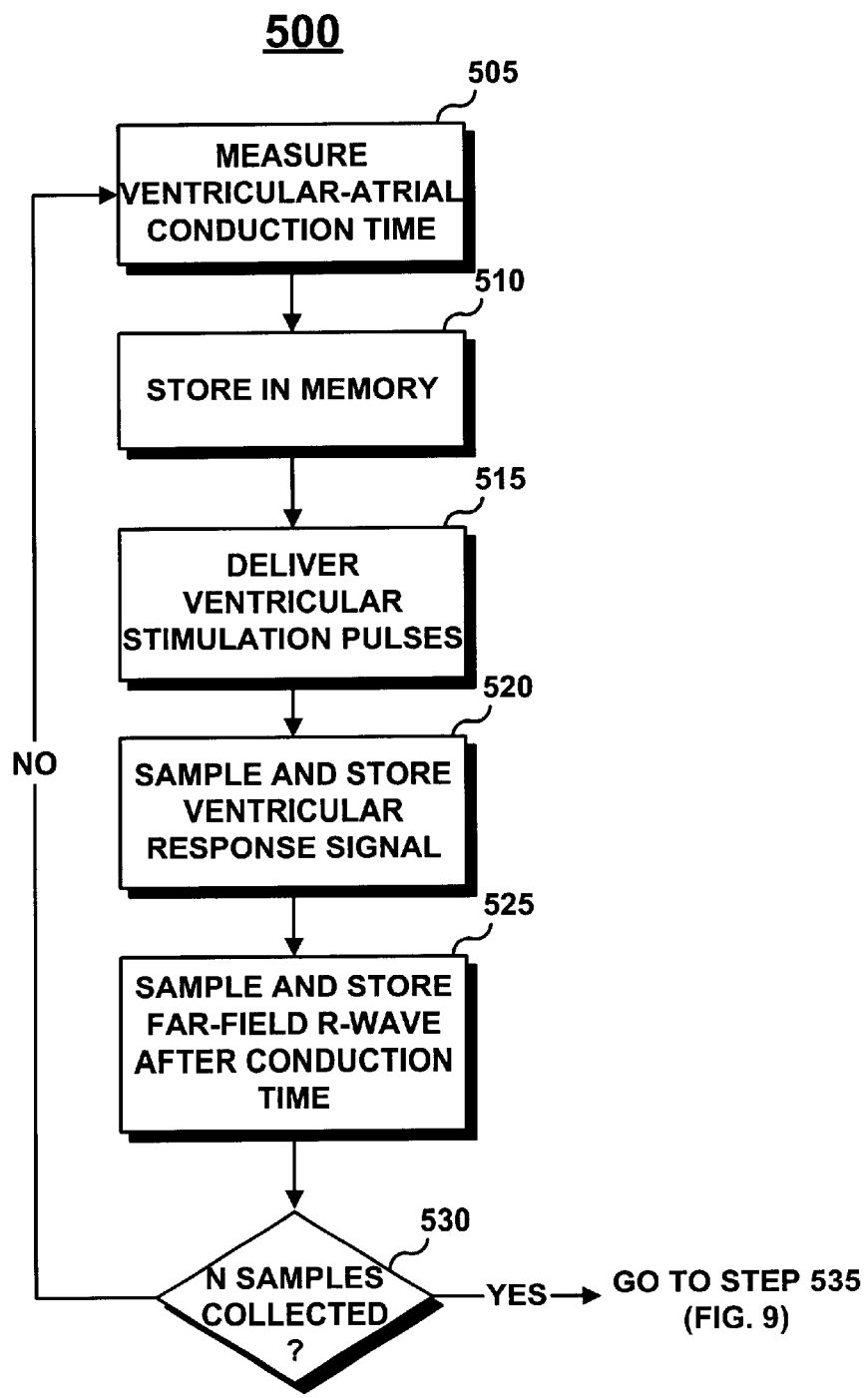
FIG. 8 is a flow chart depicting a method for obtaining and storing conduction time measurements, far-field signals, and ventricular response signals.
Figure 9:
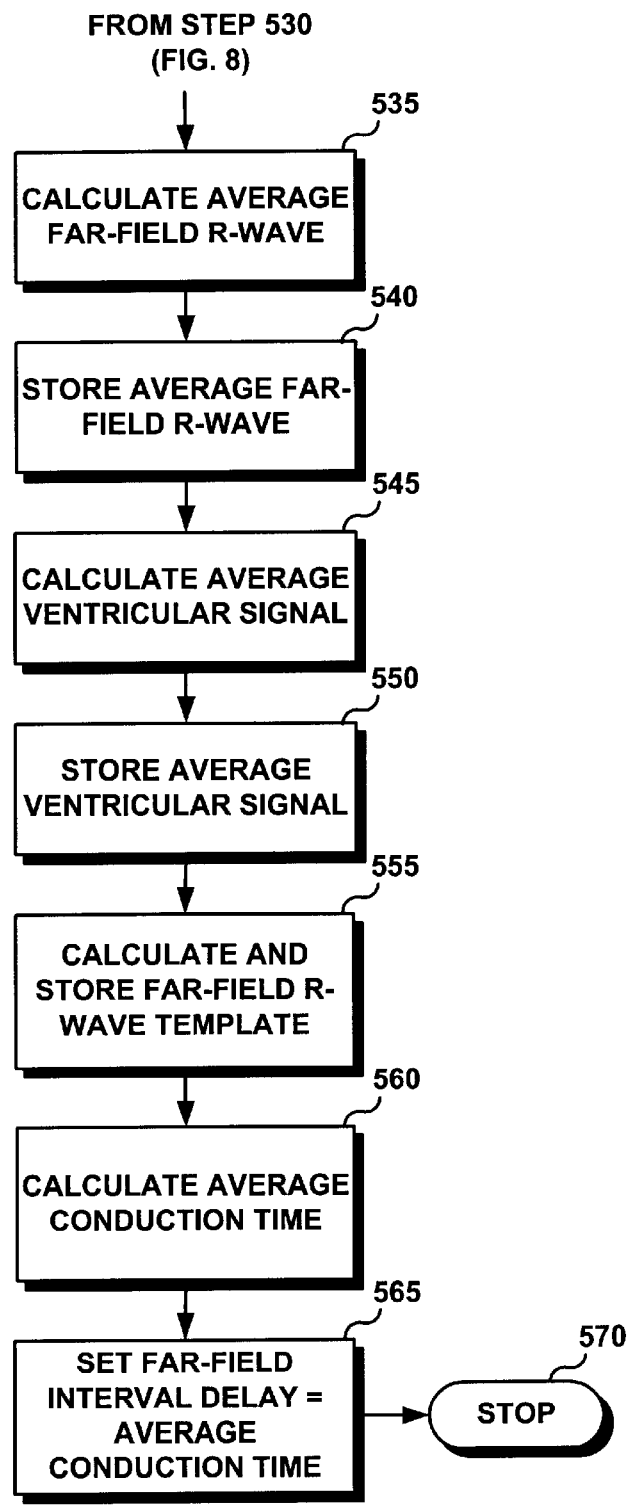
FIG. 9 is a flow chart depicting a method for determining an average far-field interval delay and average far-field signal template, from the measurements obtained in the methods of FIG. 7 and to be used in the capture verification methods of FIG. 3.

Now referring to FIG. 8, method 500 called upon by method 400 for determining a far-field R-wave template and the far-field interval window is illustrated. At step 505, the conduction time between the stimulation site in the ventricle (s) and the far-field sensing site is measured. If far-field sensing is performed in an atrium, then a ventricular-atrial conduction time is measured as indicated in step 505. If far-field sensing is performed in the opposing ventricle during left-only or right-only ventricular stimulation, then the conduction time measured at step 505 is the interventricular conduction time. The measured conduction time is stored in memory 94 at step 510.

At step 515, the ventricular stimulation is delivered; either biventricular, right ventricular or left ventricular stimulation is delivered depending on which step of method 400 called upon method 500 for determining a far-field R-wave template. At step 520, the ventricular response signal is sampled and stored at step 520. The ventricular response signal is the signal detected locally, at the stimulation site. At step 525, the far-field signal is sampled and stored following each ventricular stimulation pulse starting at a time approximately equal to the measured conduction time.

At decision step 530, if a desired number (N) of sampled signals and conduction time measurements have not yet been stored in memory 94, the method 500 returns to step 505 to repeat the conduction time measurement and the collection of a ventricular response signal and a far-field R-wave signal. A predetermined number (N) of samples, for example five samples, should be collected to allow an average conduction time and average far-field R-wave signal to be calculated as will be described next.

Once the desired number of samples are collected and stored in memory 94, method 500 continues to step 535 (FIG. 9) to calculate an average far-field R-wave signal from the stored far-field signal samples. At step 540, the average far-field R-wave is stored in memory 94. At step 545, the average ventricular response signal is calculated from the stored ventricular response signal samples, and the average ventricular response is stored in memory at step 550.

At step 555, the far-field R-wave template is calculated by subtracting the average ventricular response signal from the average far-field R-wave. This far-field R-wave template is also stored in memory 94 and will be used during ventricular capture verification method 300 as previously described.

At step 560, the average conduction time is calculated from the stored conduction times measured between the stimulation site(s) and the far-field signal sensing site. The far-field interval window delay is set equal to the average conduction time at step 565. Thus, during the ventricular capture verification method 300, the far-field interval window will begin at a time approximately equal to the conduction time between the stimulated site(s) and far-field sensing site. At step 570, the method 500 is terminated, and the automatic determination of the far-field R-wave template and the far-field interval delay is complete.

Thus, a multichamber cardiac stimulation device has been described which includes automatic ventricular capture verification using far-field R-wave sensing. This method of ventricular capture verification advantageously overcomes the problems normally encountered in evoked response sensing, such as lead polarization, by sensing for the far-field R-wave at a location away from the stimulation site and later in time than the stimulation pulse. Thus, the methods of the present invention allow reliable automatic capture verification to be realized in a multichamber cardiac stimulation device whereby patient safety and device performance are improved. These advantages are further realized without additional hardware or sensing circuitry. One skilled in the art will appreciate that the present invention can be practice by other than the described embodiments, which are presented for purposes of illustration and are not intended to be exclusive.

What is claimed is:

1. A method of verifying ventricular capture in a first ventricle, the method comprising:
   delivering a ventricular stimulation pulse to the first ventricle;
   monitoring far-field evoked responses on two atrial channels; and
   verifying ventricular capture in the first ventricle by detecting the far-field evoked responses on the two atrial channels during a far-field interval window following the delivery of the ventricular stimulation pulse in the first ventricle.

2. The method of claim 1, further comprising verifying ventricular capture of a second ventricle by:
   delivering a ventricular stimulation pulse to the second ventricle; and
   verifying ventricular capture in the second ventricle by detecting the far-field evoked responses on the two atrial channels during the far-field interval window following the delivery of the ventricular stimulation pulse to the second ventricle.

3. The method of claim 1, wherein verifying ventricular capture in the first ventricle comprises comparing the far-field evoked responses to a ventricular far-field signal recognition template that is expected to follow successful ventricular capture.

4. The method of claim 3, wherein comparing the far-field evoked responses to the ventricular far-field signal recognition template comprises comparing the far-field evoked responses to a far-field R-wave template.

5. The method of claim 3, further comprising confirming ventricular capture when the far-field evoked responses correspond approximately to the ventricular far-field signal recognition template.

6. The method of claim 5, further comprising automatically generating the ventricular far-field signal recognition template by averaging a number of far-field R-wave signals that are sampled following the delivery of a plurality of ventricular stimulation pulses.

7. The method of claim 3, wherein comparing the far-field evoked responses to the ventricular far-field signal recognition template comprises comparing a characteristic of the far-field evoked responses to any one or more characteristics of the ventricular far-field signal recognition template:
   a peak amplitude;
   a maximum slope;
   a minimum slope; and
   an integral.

8. The method of claim 7, further comprising confirming ventricular capture if a characteristic of the far-field evoked responses approximately equals a characteristic of the ventricular far-field signal.

9. The method of claim 1, further comprising setting the far-field interval window during which a far-field R-wave is expected to occur following the delivery of a ventricular stimulation pulse.

10. The method of claim 9, wherein setting the far-field interval window comprises initiating the far-field interval window after a predetermined delay following the delivery of the ventricular stimulation pulse.

11. The method of claim 10, further comprising setting the predetermined delay equal to a ventricular-atrial (VA) conduction time.

12. The method of claim 10, further comprising setting the predetermined delay equal to the average time measured from a number of ventricular stimulation pulses to a plurality of far-field R-waves detected on the two atrial channels.

13. The method of claim 1, wherein verifying ventricular capture in the first ventricle comprises detecting an atrial signal during the far-field interval window.

14. The method of claim 1, wherein verifying ventricular capture in the first ventricle comprises detecting a right ventricular signal during the farfield interval window if a ventricular stimulation pulse has been delivered only in a left ventricle.

15. The method of claim 1, wherein verifying ventricular capture in the first ventricle comprises detecting a left ventricular signal during the far-field interval window if a ventricular stimulation pulse has been delivered only in a right ventricle.

16. The method of claim 1, further comprising triggering the delivery of a safety, backup stimulation pulse in the first ventricle if ventricular capture is not confirmed.

17. The method of claim 1, further comprising triggering a threshold test in the first ventricle if ventricular capture is not confirmed.

18. A method of verifying ventricular capture in a first ventricle, the method comprising:
   delivering a bi-ventricular stimulation to the first ventricle and to a second ventricle;
   monitoring a far-field evoked response on an atrial channel resulting from the bi-ventricular stimulation; and
   verifying ventricular capture in the first ventricle by detecting the resulting far-field evoked response on the atrial channel during a far-field interval window following the delivery of the ventricular stimulation pulse in the first ventricle.

19. The method of claim 18, further comprising verifying ventricular capture of a second ventricle by detecting the resulting far-field evoked response on the atrial channel during a far-field interval window following the delivery of the ventricular stimulation pulse in the second ventricle.

20. The method of claim 19, wherein verifying capture in the first and second ventricles comprises detecting far-field evoked responses on two atrial channels during the far-field interval window following the delivery of the ventricular stimulation pulse in any one of the first or the second ventricle.

21. A multi-chamber stimulation device that verifies ventricular capture in a first ventricle, the device comprising:
   a pulse generator that generates stimulation pulses;
   a lead connected to the pulse generator that delivers a ventricular stimulation pulse to the first ventricle;
   an atrial sensor assembly that monitors far-field evoked responses on two atrial channels; and
   a controller that is in communication with the sensor assembly and that is operative to verify ventricular capture in the first ventricle by detecting the far-field evoked responses on the two atrial channels during a far-field interval window following the delivery of the ventricular stimulation pulse in the first ventricle.

22. The stimulation device of claim 21, wherein the controller verifies ventricular capture of a second ventricle by detecting the far-field evoked responses on the two atrial channels during the far-field interval window following the delivery of a ventricular stimulation pulse to the second ventricle.

23. The stimulation device of claim 21, wherein the controller verifies ventricular capture in the first ventricle by comparing the far-field evoked responses to a biventricular far-field signal recognition template that is expected to follow successful ventricular capture.

24. The stimulation device of claim 23, wherein the biventricular farfield signal recognition template comprises a far-field R-wave template.

25. The stimulation device of claim 23, wherein the controller verifies ventricular capture if the far-field evoked responses correspond approximately to the biventricular far-field signal recognition template.

26. The stimulation device of claim 25, wherein the biventricular far-field signal recognition template results from the average of a plurality of far-field R-wave signals that are sampled following the delivery of a plurality of ventricular stimulation pulses.

27. The stimulation device of claim 23, wherein the controller confirms ventricular capture if a characteristic of the far-field evoked responses corresponds to any one or more characteristics of the biventricular farfield signal recognition template:
   a peak amplitude;
   a maximum slope;
   a minimum slope; and
   an integral.

28. The stimulation device of claim 21, wherein the far-field interval window is initiated during a period in which a far-field R-wave is expected to occur following the delivery of a ventricular stimulation pulse.

29. The stimulation device of claim 28, wherein the far-field interval window is initiated after a predetermined delay following the delivery of the ventricular stimulation pulse.

30. The stimulation device of claim 29, wherein the predetermined delay is substantially equal to a ventricular-atrial (VA) conduction time.

31. The stimulation device of claim 29, wherein the predetermined delay is substantially equal to the average time measured from a number of ventricular stimulation pulses to a plurality of far-field R-waves detected on the two atrial channels.

32. A multi-chamber stimulation device that verifies ventricular capture in a first ventricle, the device comprising:
   a pulse generator that generates stimulation pulses;
   a lead connected to the pulse generator that delivers a bi-ventricular stimulation to the first ventricle and to a second ventricle;
   an atrial sensor that monitors a far-field evoked response on an atrial channel resulting from the bi-ventricular stimulation; and
   a controller in communication with the sensor and that is operative to verify ventricular capture in the first ventricle by detecting the resulting far-field evoked response on the atrial channel during a far-field interval window following the delivery of the ventricular stimulation pulse in the first ventricle.

33. The stimulation device of claim 32, wherein the controller verifies ventricular capture of a second ventricle by detecting the far-field evoked response on the atrial channel during a far-field interval window following the delivery of the ventricular stimulation pulse in the second ventricle.

34. The stimulation device of claim 33, wherein the controller verifies ventricular capture in the first and second ventricles by detecting far-field evoked responses on two atrial channels during the far-field interval window following the delivery of the ventricular stimulation pulse in any one of the first or the second ventricle.

35. A multi-chamber stimulation device that verifies ventricular capture in a first ventricle, comprising:
   means for delivering a stimulation pulse to the first ventricle;
   means for monitoring a far-field evoked response on a pair of atrial channels corresponding to the two atria; and
   means for verifying capture in the first ventricle by detecting the far-field evoked response on the atrial channels during a farfield interval window following the delivery of the ventricular stimulation pulse in the first ventricle.

36. The stimulation device of claim 35, further comprising means for verifying ventricular capture of a second ventricle.

37. The stimulation device of claim 36, wherein the means for verifying ventricular capture of the second ventricle comprises:
   means for delivering a ventricular stimulation pulse to the second ventricle; and
   means for verifying ventricular capture in the second ventricle by detecting the far-field evoked responses on the one or more atrial channels during the far-field interval window following the delivery of the ventricular stimulation pulse to the second ventricle.

38. The stimulation device of claim 35, wherein the means for verifying ventricular capture in the first ventricle compares the far-field evoked responses to a biventricular far-field signal recognition template that is expected to follow successful ventricular capture.

39. The stimulation device of claim 35, wherein the biventricular far-field signal recognition template comprises a far-field R-wave template.

40. A multi-chamber stimulation device that verifies capture in a first ventricle, comprising:
   means for delivering a bi-ventricular stimulation to the first ventricle and to a second ventricle;

means for monitoring a far-field evoked response on an atrial channel resulting from the bi-ventricular stimulation; and means for verifying capture in the first ventricle by detecting the resulting far-field evoked response on the atrial channel during a far-field interval window following the delivery of the ventricular stimulation pulse in the first ventricle.

41. The stimulation device of claim 40, further comprising means for verifying capture of a second ventricle.

42. The stimulation device of claim 41, wherein the means for verifying capture of the second ventricle comprises means for detecting the far-field evoked response on the atrial channel during a far-field interval window following the delivery of the ventricular stimulation pulse in the second ventricle.

43. The stimulation device of claim 42, wherein the means for verifying capture of the first and second ventricles comprises means for detecting far-field evoked responses on two atrial channels during the far-field interval window following the delivery of the ventricular stimulation pulse in any one of the first or the second ventricle.

* * * * *